(12) United States Patent
Kleven et al.

(10) Patent No.: US 7,217,420 B2
(45) Date of Patent: May 15, 2007

(54) MYCOPLASMA GALLISEPTICUM FORMULATION

(75) Inventors: Stanley H. Kleven, Athens, GA (US); Naola Ferguson, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 123 days.

(21) Appl. No.: 10/194,180

(22) Filed: Jul. 13, 2002

(65) Prior Publication Data
US 2004/0009179 A1 Jan. 15, 2004

(51) Int. Cl.
*A61K 39/02* (2006.01)
*C12N 1/20* (2006.01)

(52) U.S. Cl. ............... 424/264.1; 424/184.1; 424/234.1; 435/243; 435/252.1

(58) Field of Classification Search ............. 424/184.1, 424/234.1, 264.1; 435/243, 252.1
See application file for complete search history.

(56) References Cited

U.S. PATENT DOCUMENTS

| | | | |
|---|---|---|---|
| 5,004,607 | A | 4/1991 | Ragland et al. |
| 5,064,647 | A | 11/1991 | Storm |
| 5,489,430 | A | 2/1996 | Saito et al. |
| 5,621,076 | A | 4/1997 | Kodama et al. |
| 5,766,594 | A | 6/1998 | Kodama et al. |
| 5,914,113 | A | 6/1999 | Schrier |
| 6,086,892 | A | 7/2000 | Cook |
| 6,270,770 | B1 | 8/2001 | Schrier et al. |

FOREIGN PATENT DOCUMENTS

| | | |
|---|---|---|
| EP | 0 307 976 A1 | 3/1989 |
| EP | 0 603 406 A1 | 6/1994 |
| EP | 0 692 532 A1 | 1/1996 |
| GB | 1137306 | 12/1968 |
| JP | 52 134019 | 11/1977 |
| JP | 07 133295 | 5/1995 |
| JP | 07 228542 | 8/1995 |

OTHER PUBLICATIONS

Greenspan et al. (Nature Biotechnology 7: 936-937, 1999).*
Colman, Res. Immunology, Jan. 1994, vol. 145, pp. 33-36; e.g. p. 33, col. 2.*
Marois, C., et al., "Molecular Differentiation of *Mycoplasma gallisepticum* and *Mycoplasma imitans* Strains by Pulsed-Field Gel Electrophoresis and Random Amplified Polymorphic DNA," *J. Vet. Med. B* 48:695-703, 2001.
Whithear, K.G., "Control of Avian Mycoplasmoses by Vaccination," *Rev. Sci. Tech. Off. Int. Eipz.* 15(4):1527-1553, 1996.

* cited by examiner

*Primary Examiner*—Robert A. Zeman
(74) *Attorney, Agent, or Firm*—Christensen, O'Connor Johnson Kindess PLLC

(57) ABSTRACT

The present invention provides a protective formulation that prevents virulent *Mycoplasma gallisepticum* infection in birds of the order Galliformes. The formulation comprises a protective amount of live MG strain K5054 or derivatives thereof in a pharmaceutically acceptable carrier. A vaccine that prevents virulent *Mycoplasma gallisepticum* infection in birds of the order Galliformes is also presented. Methods for administering the formulation and vaccine are also presented.

6 Claims, 10 Drawing Sheets

Figure 1:
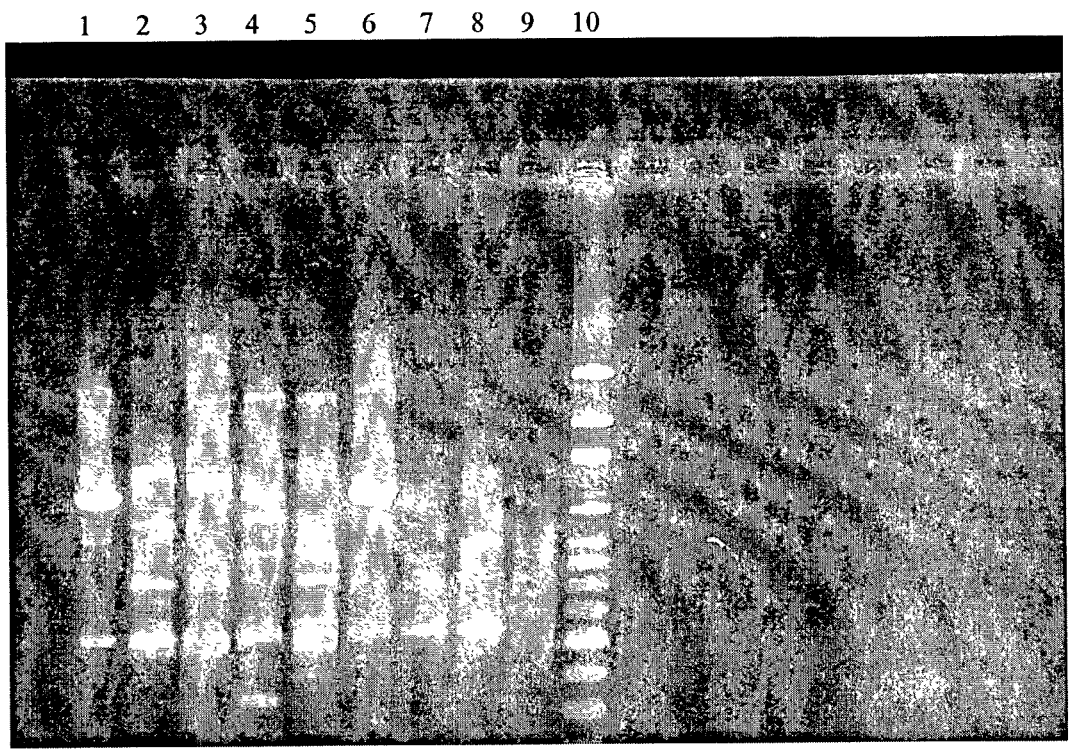

Lane 1 = R
Lane 2 = HF-51
Lane 3 = K5054
Lane 4 = ts-11
Lane 5 = 6/85
Lane 6 = F
Lane 7 = S6
Lane 8 = A5969
Lane 9 = Negative
Lane 10 = Molecular weight marker (Amresco®, 100 BP Ladder, range of fragments (100 bp-3000bp)

Lane 1 = HF-51
Lane 2 = K5054
Lane 3, 4, 5 = Unrelated field isolates
Lane 6 = R
Lane 7 = 6/85
Lane 8 = F
Lane 9 = ts-11
Lane 10 = Negative
Lane 11 = Molecular weight marker (Amresco®, 100 BP Ladder, range of fragments (100 bp-3000bp)

Lane 1 = R
Lane 2 = HF-51
Lane 3 = K5054
Lane 4 = ts-11
Lane 5 = 6/85
Lane 6 = F
Lane 7 = S6
Lane 8 = A5969
Lane 9 = Negative
Lane 10 = Molecular weight marker (Amresco®, 100 BP Ladder, range of fragments (100 bp-3000bp)

Table 1.1. Bioassay. Serological responses of turkeys at 21, 42, 56, 70 and 84 days postchallenge with K5054 sinus exudate. Principals (K5054 challenged) and contacts were mixed at 49 days postchallenge.

| | SPA | | | | | HI | | | | | | ELISA | | | | |
|---|---|---|---|---|---|---|---|---|---|---|---|---|---|---|---|---|
| | 21 DPC[A] | 42 DPC | 56 DPC | 70 DPC | 84 DPC | 21 DPC | 42 DPC | 56 DPC | 70 DPC | 84 DPC | 21 DPC | 42 DPC | 56 DPC | 70 DPC | 84 DPC |
| K5054 | 7/8[B] (1.6)[C] | 8/8 (2.3) | 8/8 (2.9) | 7/7 (1.3) | 7/8 (1.5) | 6/8 (33.6)[D] | 4/8 (28.2) | 8/8 (61.7) | 0/8 (0.0) | 4/8 (9.2) | ND | 7/8 (0.96 ± 0.56)[E] | 8/8 (1.96 ± 1.04) | 8/8 (0.96 ± 0.59) | 4/8 (0.69 ± 0.90) |
| Neg. Controls | 0/8 (0.0) | 0/8 (0.0) | | | | 0/8 (0.0) | 0/8 (0.0) | | | | ND | 0/8 (0.08 ± 0.03) | | | |
| Contacts | | | 0/8 (0.0) | 2/6 (0.3) | 1/6 (0.2) | | | 0/8 (0.0) | 0/6 (0.0) | 0/6 (0.0) | | | 0/8 (0.56 ± 0.16) | 0/6 (0.03 ± 0.06) | 0/6 (0.00 ± 0.00) |

[A] Days postchallenge.
[B] No. of positive samples/No. of tested samples (SPA: ≥1, HI: ≥40, and ELISA: ≥0.6)
[C] Mean agglutination grade (0 to 4).
[D] Geometric mean titer.
[E] S/P ratio (mean ± standard deviation (SD)); ND=not done

Figure 4

Table 1.2. Bioassay. Serological responses, lesion evaluation and rate of isolation of *M. gallisepticum* from the trachea and air sacs of principal (K5054 challenged) and contact turkeys 10 days postchallenge with R strain.

| Group | Challenge | Serology | | | Lesions | | MG Isolation | |
|---|---|---|---|---|---|---|---|---|
| | | SPA | HI | ELISA | Air sac score [A] | Mean tracheal mucosa thickness [B] | Trachea | Air sacs |
| Principals | R | 4/4[C] (2.3)[D] | 4/4 (56.6)[E] | 4/4 (2.20 $\pm$ 1.39)[F] | 0/0 ($0.0 \pm 0.0$)[G, a] | $14.44 \pm 2.68^a$ | $0/4^a$ | $0/4^a$ |
| | No challenge | ND | 3/4 (33.6) | 1/4 (0.55 $\pm$ 0.27) | 0/0 ($0.0 \pm 0.0$)$^a$ | $13.25 \pm 1.97^a$ | $0/4^a$ | $0/4^a$ |
| Contacts | R | 3/3 (2.7) | 3/3 (160.0) | 3/3 (2.31 $\pm$ 0.30) | 3/3 ($4.0 \pm 0.0$)$^b$ | $31.25 \pm 1.39^b$ | $3/3^b$ | $3/3^b$ |
| | No challenge | ND | 0/3 (0.0) | 0/3 (0.04 $\pm$ 0.01) | 0/0 ($0.0 \pm 0.0$)$^a$ | $14.33 \pm 0.63^a$ | $0/3^a$ | $0/3^a$ |

[A] Macroscopically scored from 0 to 4

[B] Mean thickness for the group in units. 1 unit = 0.0083mm

[C] No. of positive samples/No. of tested samples (SPA: $\geq 1$, HI: $\geq 40$, ELISA: $\geq 0.6$, Air sac score $\geq 1$)

[D] Mean agglutination grade (scored from 0 to 4).

[E] Geometric mean titer.

[F] S/P ratio (mean $\pm$ SD)

[G] Mean score $\pm$ SD; $^{a,b}$ Values within a column with a different lower case superscript are significantly different ($P \leq 0.05$)

Figure 5

Table 2.1. Safety. Serological responses of chickens postvaccination/challenge with ts-11, K5054 and R at 3 weeks of age

| Vaccine/ Challenge | SPA | | HI | | ELISA | |
|---|---|---|---|---|---|---|
| | 10 DPV[A] | 35 DPV | 10 DPV | 35 DPV | 10 DPV | 35 DPV |
| TS-11 | 2/16[B] (0.1)[C] | 8/10 (2.4) | 0/16[D] (0.0) | 1/10 (11.8) | 0/16[E] (0.80 ± 0.01) | 7/10 (0.86 ± 0.86) |
| K5054 | 2/16 (0.1) | 10/10 (3.0) | 0/16 (0.0) | 3/10 (24.6) | 1/16 (0.33 5.08) | 3/10 (0.32 ± 0.19) |
| R | 15/15 (3.0) | N/A | 5/15 (20.6) | N/A | 11/15 (0.87 ± 0.73) | N/A |
| Neg. Controls | 0/16 (0.0) | 0/5 (0.0) | 0/16 (0.0) | 0/5 (0.0) | 0/16 (0.44 ± 0.01) | 0/5 (0.19 ± 0.01) |

[A] Days postchallenge.
[B] No. of positive samples/No. of tested samples (SPA: ≥1, HI: ≥40, and ELISA: ≥ 0.6)
[C] Mean agglutination grade (0 to 4).
[D] Geometric mean titer.
[E] S/P ratio (mean ± standard deviation (SD)); N/A - not applicable

Figure 6

Table 2.2. Safety. Lesion scores and rate of *M.gallisepticum* isolation from chickens 10 days postvaccination/challenge with ts-11, K5054 and R at 3 weeks of age.

| Vaccine/Challenge Strain | Air Sac Lesion Score[A] | Mean tracheal mucosal thickness[B] | MG Isolation Trachea | MG Isolation Air sacs |
|---|---|---|---|---|
| TS-11 | 0/16[C] (0.0 ± 0.0)[D,a] | 6.38 ± 1.77[a] | 1/16 | 0/16 |
| K5054 | 0/16 (0.0 ± 0.0)[a] | 5.94 ± 1.77[a] | 16/16 | 6/16 |
| R | 12/15 (1.8 ± 1.15)[b] | 42.75 ± 1.83[b] | 15/15 | 15/15 |
| Neg. Controls | 0/16 (0.0 ± 0.0)[a] | 6.23 ± 1.77[a] | 0/16 | 0/16 |

[A] Macroscopically scored from 0 to 4

[B] Mean thickness for the group in units. 1 unit = 0.0083mm

[C] No. of positive samples/No. of tested samples (Air sac score ≥ 1)

[D] Mean score ± SD

[a,b] Values within a column with a different lower case superscript are significantly different ($P \leq 0.05$)

Figure 7

Table 2.3. Safety. Serological responses, lesion scores and rate of *M.gallisepticum* isolation from turkeys 10 days post vaccination/challenge with K5054 and R at 4 weeks of age.

| Group | Serology | | | Lesions | | MG Isolation | |
|---|---|---|---|---|---|---|---|
| | SPA | HI | ELISA | Air Sac Lesion Score[A] | Mean tracheal mucosal thickness[B] | Trachea | Air sacs |
| K5054 | 0/15[C] (0.0)[D] | 0/15 (0.0)[E] | 0/15 (0.44 ± 0.01)[F] | 2/15 (0.2 ± 0.7)[G,a] | 12.77 ± 2.52[a] | 15/15 | 13/15 |
| R | 15/15 (3.1) | 0/15 (2.2) | 3/15 (0.24 ± 0.49) | 13/15 (2.2 ± 1.3)[b] | 20.87 ± 4.36[b] | 15/15 | 15/15 |
| Neg. Controls | 0/14 (0.0) | 0/14 (0.0) | 0/14 (0.68 ± 0.05) | 0/14 (0.0 ± 0.0)[a] | 8.29 ± 1.02[a] | 0/14 | 0/14 |

[A] Macroscopically scored from 0 to 4
[B] Mean thickness for the group in units. 1 unit = 0.0083mm
[C] No. of positive samples/No. of tested samples (Air sac score ≥ 1, SPA: ≥1, HI: ≥40, and ELISA: ≥ 0.6)
[D] Mean agglutination grade (0 to 4).
[E] Geometric mean titer.
[F] S/P ratio (mean ± standard deviation (SD))
[G] Mean score ± SD
[a,b] Values within a column with a different lower case superscript are significantly different ($P \leq 0.05$)

Figure 8

Table 3.1. Efficacy. Experiment 2. Serological responses of chickens 10 days post challenge with R strain of MG.

| Group | Challenge | Serology | | | Lesions | | MG Isolation | |
|---|---|---|---|---|---|---|---|---|
| | | SPA | HI | ELISA | Air Sac Lesion Scores[A] | Mean tracheal mucosal thickness[B] | Trachea | Air sacs |
| TS-11 | R | 38/38[C] (4.0)[D] | 37/38 (43.8)[E] | 38/38 (4.64 ± 1.06)[F] | 17/38 (0.7 ± 1.0)[G,a] | 16.32 ± 19.27[a] | 38/38 | 33/38 |
| | No challenge | 9/9 (3.8) | 0/9 (20.0) | 8/9 (1.33 ± 0.75) | 0/9 (0.0 ± 0.0)[b] | 7.28 ± 1.77[a] | 5/9 | 0/9 |
| K5054 | R | 39/39 (4.0) | 32/39 (37.3) | 39/39 (2.88 ± 1.14) | 13/39 (0.4 ± 0.5)[a] | 8.88 ± 2.91[a] | 39/39 | 36/39 |
| | No challenge | 10/10 (4.0) | 1/10 (15.9) | 10/10 (1.32 ± 0.44) | 0/10 (0.0 ± 0.0)[b] | 7.50 ± 1.72[a] | 10/10 | 0/10 |
| No Vaccine | R | 40/40 (4.0) | 33/38 (36.5) | 40/40 (3.38 ± 1.02) | 40/40 (2.9 ± 0.4)[c] | 57.23 ± 22.17[b] | 40/40 | 40/40 |
| | No challenge | 0/32 (0.0) | 0/32 (0.0) | 0/32 (0.13 ± 0.05) | 0/32 (0.0 ± 0.0)[b] | 6.94 ± 1.42[a] | 0/32 | 0/31 |

[A] Macroscopically scored from 0 to 4
[B] Mean thickness for the group in units. 1 unit = 0.0083mm
[C] No. of positive samples/No. of tested samples (Air sac score ≥ 1, SPA: ≥1, HI: ≥40, and ELISA: ≥ 0.6)
[D] Mean agglutination grade (0 to 4).
[E] Geometric mean titer.
[F] S/P ratio (geometric mean ± standard deviation (SD))
[G] Mean score ± SD
[a,b] Values within a column with a different lower case superscript are significantly different ($P \leq 0.05$)

Figure 9

Table 3.2. Efficacy. Serological responses, lesion scores and rate of isolation of *M. gallisepticum* from turkeys 10 days post challenge with R strain at 6 weeks post vaccination.

| Group | Serology | | | Air Sac Lesion Scores[A] | Mean trac

SEQUENCE LISTING

<160> NUMBER OF SEQ ID NOS: 8

<210> SEQ ID NO 1
<211> LENGTH: 570
<212> TYPE: DNA
<213> ORGANISM: Mycoplasma gallisepticum

<400> SEQUENCE: 1

```
ctgaagttaa gactgaacaa ttaattggca cacaattagt aacaactgat gtagctagca      60
ctcaagctgt aggtactgaa gaagttcaag gtgttttatt acctcctagt caacaaccaa     120
cggaaatgcg tccagctcct tcaccaatgg gtagtcctaa gttattaggt ccaaaccaag     180
ctggtcatcc acaacacgga ccacgtccga tgaatgctca tccaggtcaa ccacgtcctc     240
aacaagctgg cccacgtcca atgggagctg gtggatctaa ccaaccaaga ccaatgccaa     300
atggtccaca aaacccacaa ggtccacgac caatgaaccc tcaaggcaat cctcgtcctg     360
gaccagctgg ccaacgacct aacggcccac aaaattctca accacgtcct caacaagctg     420
gcccacgtcc aatgggagct ggtagatcta accaaccaag accaatgcca atggtccac      480
aaaaacaaca aggtccaaga ccaatgaacc ctgaaggcaa tcctcgtcct caaccagctg     540
gtgtcagacc taacagccca caagctacca                                      570
```

<210> SEQ ID NO 2
<211> LENGTH: 698
<212> TYPE: DNA
<213> ORGANISM: Mycoplasma gallisepticum

<400> SEQUENCE: 2

```
cgagaaaata agaacttact agcgttcata tttttactca tgacattcgt tgatgaatta      60
tctgatttcg aagaatcaac tgtcttcatc ccatttcatt caaagatttc gtggatatct     120
ttagttccag ctgctaaatc tgcataagca ttgtaatatg gatcagtagt tcgattcgtt     180
tcacctgttt ttaataatga attattagta atcttttgtg agtaggtgtt ggctgtgtta     240
ccatttccct tagctctaat gaaattattc atcagattga tctcatcaat atctgattga     300
attacaccaa cgttatcacg gttagtatta ttagtttgtt ttaaatattg ttgaacataa     360
gctgcactaa atgatacgtc aaaactatta aacatatcag aagcagtcat taacaactta     420
ccaccagaat ctgatgataa gttgttggga atattaatcc ctttagttgt actatttaca     480
taactgtcca accctctagt aatgaattgg ttataagctc tcatcccctt gttttcatca     540
aaaggttggt ctttgggatt tttaaatgct tggaaattat aacttgctac taatgctgtt     600
gagctaaacag tacgatcatt aaagatcgaa tttagtccat cttaggagt atcgctggta     660
aaaacaattc ttgaaactaa attagggttt tcatcagt                              698
```

<210> SEQ ID NO 3
<211> LENGTH: 334
<212> TYPE: DNA
<213> ORGANISM: Mycoplasma gallisepticum

<400> SEQUENCE: 3

```
tttctagcgc tttagcccta aaccctaacc gaattactaa cccattaatg aatagagata      60
acgtaatcgg tcaaggtgcg ttcattagta gaaatgatat tccatcatca ttctttgaaa     120
acaaaattaa tgatattgta actacagaag ctgatggtaa agaagtatta gatagtaaat     180
acattaattc aatctataga tatactccac ctcaaaacaa tcctgatatt agattaagat     240
```

-continued

```
tattagtaat tgatcgttct agagcaacta atgacttcat taagttatta cctcaagtat        300
tagttgatgg cgaatacgtt gctgttccac aaga                                    334

<210> SEQ ID NO 4
<211> LENGTH: 10
<212> TYPE: DNA
<213> ORGANISM: Mycoplasma gallisepticum

<400> SEQUENCE: 4
cccgtcagca                                                                10

<210> SEQ ID NO 5
<211> LENGTH: 17
<212> TYPE: DNA
<213> ORGANISM: Mycoplasma gallisepticum

<400> SEQUENCE: 5
aggcagcagt agggaat                                                        17

<210> SEQ ID NO 6
<211> LENGTH: 13
<212> TYPE: DNA
<213> ORGANISM: Mycoplasma gallisepticum

<400> SEQUENCE: 6
gtaaaacgac ggc                                                            13

<210> SEQ ID NO 7
<211> LENGTH: 20
<212> TYPE: DNA
<213> ORGANISM: Mycoplasma gallisepticum

<400> SEQUENCE: 7
cataactaac ataagggcaa                                                     20

<210> SEQ ID NO 8
<211> LENGTH: 10
<212> TYPE: DNA
<213> ORGANISM: Mycoplasma gallisepticum

<400> SEQUENCE: 8
ccgcagccaa                                                                10
```

MYCOPLASMA GALLISEPTICUM FORMULATION

BACKGROUND OF THE INVENTION (1) Field of the Invention

The present invention relates generally to poultry protection, in particular to a *Mycoplasma gallisepticum* (MG) protective formulation.

(2) Description of the Prior Art

*Mycoplasma gallisepticum*, a pathogen of the avian respiratory tract, belongs to the class Mollicutes, order Mycoplasmatales, and family Mycoplasmataceae. Under certain circumstances, MG may be associated with acute respiratory disease in chickens and turkeys, especially in young birds, with the turkey being more susceptible. It can also cause upper respiratory disease in game birds. Edematous changes early in infection indicate an immunopathological response may be responsible for some of the pathology observed. More recently it has been recognized as a cause of conjunctivitis in house finches in North America. The severity of the disease is greatly affected by the degree of secondary infection with viruses such as Newcastle disease and infectious bronchitis, and/or bacteria such as *Escherichia coli*. A more chronic form of the disease may occur and can cause reduced egg production in breeders and layers. The infection is spread vertically through infected eggs and horizontally by close contact. Other methods of spread are less well documented. MG can be detected in two ways. The presence of MG can be confirmed by isolating the organism in a cell-free medium or by detecting its DNA directly in infected tissues or swab samples. When results are equivocal, chicken embryos or chickens may be inoculated with suspect material. Infection is diagnosed by demonstration of the organism or its DNA or by the detection of specific humoral antibodies.

Samples for isolation consist of swabs of organs or tissues, exudates or diluted tissue homogenates. Culture may also be attempted from aspirates from the infraorbital sinuses or joint cavities and from yolk or embryos. The sample selected will be influenced by the clinical signs and by any lesions present. Broth and agar are used for isolation, but it is normally necessary to obtain mycoplasma colonies on agar before attempting identification. If there is difficulty, an initial passage of the material through mycoplasma-free chicken embryos or mycoplasma-free chickens may be helpful.

Although some basic biochemical tests can be helpful in preliminary classification of mycoplasma isolates, final identification must be by serological or DNA tests. The most satisfactory of these are PCR, the fluorescent antibody test, and the immunoperoxidase test.

DNA detection methods, mainly based on the polymerase chain reaction, have come into use in specialized laboratories. A commercial kit has been marketed in several countries and can be used to detect field strains and to distinguish them from the vaccine F strain.

Several serological tests have been used to detect MG antibodies, but specificity and sensitivity have been lacking to some degree in all of them. They are more satisfactory for flock screening than for testing individual birds. The most commonly used are the rapid serum agglutination (RSA) test, the enzyme-linked immunosorbent assay (ELISA) and the hemagglutination inhibition (HI) test. In the RSA test, sera from individual birds are tested for agglutination using commercially produced stained MG antigen. Chicken or turkey sera that yield agglutination reactions with the antigen within 2 minutes should be heated at 56° C. for 30 minutes and retested. Sera that still react, especially when diluted, are considered to be positive. These may then be confirmed by an ELISA or a HI test.

*Mycoplasma gallisepticum* (MG) can cause significant economic loss in chickens and turkeys due to chronic respiratory disease, downgrading of carcasses in meat-type birds and loss of production in layers. Sporadic outbreaks, having important economic consequences, occur in turkeys and broiler chickens, and remain a costly enzootic infection in commercial egg layers.

Although the preferred method of MG control is maintenance of MG-free flocks, both live and inactivated vaccines have been used.

Vaccines can, in principle, be divided into two groups, i.e. live (attenuated) vaccines and inactivated vaccines. The advantages of live vaccines include the presentation of all the relevant immunogenic determinants of an infectious agent in its natural form to the host's immune system, and the necessity of a relatively small amount of the immunizing agent, because of its inherent property to multiply in the vaccinated host. A major disadvantage of a live vaccine is a concern with its safety: a live vaccine may induce disease (in immuno-compromised) animals, or the live microorganism may even revert to virulence, as a result of which animals experience a virulent infection.

The disadvantage concerning the safety aspect is not displayed by inactivated vaccines and, hence, constitutes the major advantage over live vaccines. However, a major disadvantage of inactivated vaccines is represented by their intrinsically low immunogenicity, i.e. inactivated immunogens as such have a limited ability to trigger the host's immune system. Therefore, appropriate means are necessary to augment the immunogenicity of these inactivated immunogens. This type of vaccine normally requires adjuvants with significant immunostimulatory capabilities to reach a minimum potential in preventing disease. Thus, the desirability of additional immunostimulators for use in combination with inactivated immunogens in order to augment their inherently low immunogenicity is evident, in particular immunostimulators which are applicable to more than one immunogen.

MG vaccines represent an unusual situation in that they are not recognized for general widespread use in poultry. They are generally used in birds of multiple-aged egg-layer sites to prevent egg production losses caused by wild-type strains. This is important because once the MG infection is present in a flock it remains permanently. Currently ⅔ of commercial layers are vaccinated in the United States. Internationally, there is high demand for live vaccines. In countries such as Australia the entire broiler breeder replacement stock is vaccinated using live vaccines.

In current practice, prophylactic immunization of fowl against MG related disease involves either controlled exposure to attenuated vaccine strains, or the use of inactivated, whole cell oil emulsion vaccines. Each of these approaches has certain disadvantages. For example, live vaccines can produce disease or impair reproductive function. Inactivated vaccines, while generally effective in preventing disease in immunized birds, do not reliably prevent infection, and may allow spread of infection and disease to unvaccinated birds.

In the US, vaccination is generally used only on multi-age sites where it is inevitable that flocks will become infected. The usual purpose of vaccination is to prevent egg production losses in commercial layers, although vaccines may also be used to reduce the level of egg transmission in breeding stock or as a tool for MG eradication on multi-age production sites. It is important for either live or killed vaccine to be administered before the flock is exposed to field infection with MG.

Available live vaccines are generally produced from the F strain of MG, and, more recently, strains ts-11 and 6/85, which are nonpathogenic strains with improved safety characteristics. Administration of the F strain by the intranasal or eyedrop route is preferred, but aerosol or drinking water administration may be used. The eyedrop method is recommended forts-11, while a fine spray is recommended for 6/85. Pullets are generally vaccinated between 12 and 16 weeks of age. A single dose is sufficient and vaccinated birds remain permanent carriers. Long-term use of the F strain on a multi-age site results in displacement of the field strain with the vaccine strain. F strain displaces virulent wild-type MG strains more efficiently than 6/85 or ts-11, but ts-11 has been successfully used to eradicate F strain MG in multi-age commercial layers. Multi-age production sites are also known to test serologically negative for MG after long-term use of 6/85. The F strain is fully virulent for turkeys.

U.S. Pat. No. 5,064,647 issued on Nov. 12, 1991, to Paul K. Storm is directed to a Mycoplasma vaccine based on the 6/85 strain. The 6/85 strain is attenuated by serial passage in media. For chickens it is extremely attenuated. While 6/85 may be used effectively in chickens it does not retain its attenuated state in turkeys.

Ts-11, on the other hand, is a temperature-sensitive mutant that has been chemically mutagenized. It is used universally in Australia, Latin America and Asia. It is also used in ⅔ of the United States market. Like 6/85, ts-11 is useful for vaccination of chickens against MG but not useful for vaccinating turkeys.

Current live MG vaccines are thus problematic. F-strain is virulent in turkeys. And attenuation of both 6/85 and ts-11 is unstable because the vaccine strains have unstable genomes that revert to virulent disease-causing wild-type. But, over time the turkeys outgrow the vaccines and the virulent field MG infection takes over. As such current live MG vaccines are not permitted in states such as North Carolina and Minnesota with large turkey populations. The country of Israel, as well, disallows the use of live MG vaccines.

Also, the 6/85 and ts-11 strains do not persist in chickens. In fact, prior art teaches away from persistence as a protective mechanism. U.S. Pat. No. 5,064,647 issued to Paul K Storm on Nov. 12, 1991 teaches that a benefit of strain 685 is that the strain is no longer detectable in chickens 4 weeks after inoculation. Eventually the wild-type strain returns causing disease and loss of production. On the other hand, less attenuated live vaccine strains do not adequately prevent the disease. Thus there appears to be an inverse relationship between persistence of the vaccination and mildness of the disease.

An alternative to vaccination with live organisms for preventing MG is the use of bacterins. Bacterins consist of a concentrated suspension of MG organisms in an oil emulsion. These are ordinarily administered to growing pullets at 12-16 weeks of age. They are administered parenterally, usually subcutaneously in the neck. Although two doses are desirable, a single dose is usually given because of cost and labor considerations. Bacterins are effective in preventing egg-production losses and respiratory disease, but they do not prevent infection with wild-type MG.

Thus, there remains a need for a safe and efficacious formulation to protect birds susceptible to MG. Optimally the formulation should include a live strain that persists yet causes minimal pathology in both chickens and turkeys. The protective formulation should also be stable and non-virulent in turkeys. The present invention solves this longstanding need.

SUMMARY OF THE INVENTION

The present invention is directed to a vaccine having an MG protective formulation formed from the MG strain K5054 deposited on Jun. 27, 2002, at the American Type Culture Collection (ATCC) 10801 University Boulevard., Manassas, Va. 20110-2209, Patent Deposit Designation PTA-4507, for application to birds of the Galliformes order. In a preferred embodiment, a protective amount is administered to a bird. Thus one aspect of the present invention is to provide a protective formulation for birds of the order Galliformes comprising a protective amount of a *Mycoplasma gallisepticum* bacterial strain having a RAPD pattern substantially corresponding to at least one of the band patterns of K5054, as deposited at the ATCC, as shown in FIGS. 1, 2, and 3, wherein the band pattern of K5054 in FIG. 1 is generated using as a primer SEQ ID NO:4, wherein the band pattern of K5054 is generated using as primers SEQ ID NO:5, SEQ ID NO:6, and SEQ ID NO:7, wherein the band pattern of K5054 is generated using as a primer SEQ ID NO:8, and a pharmaceutically acceptable carrier.

Figure 2:
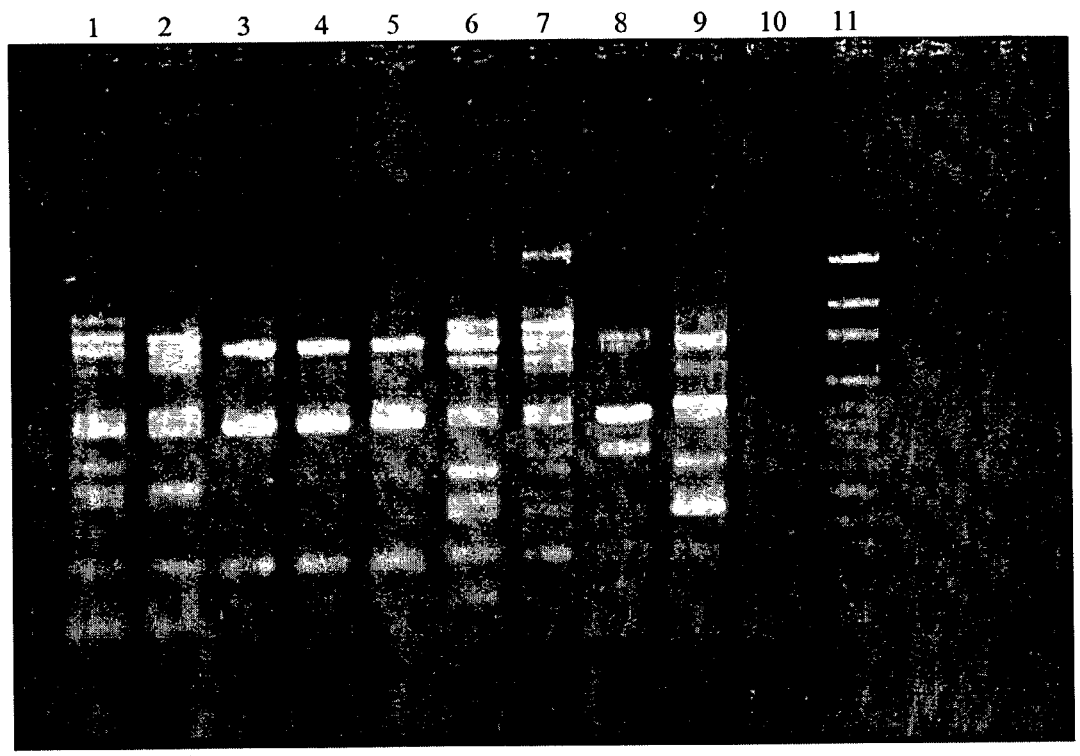
Figure 3:
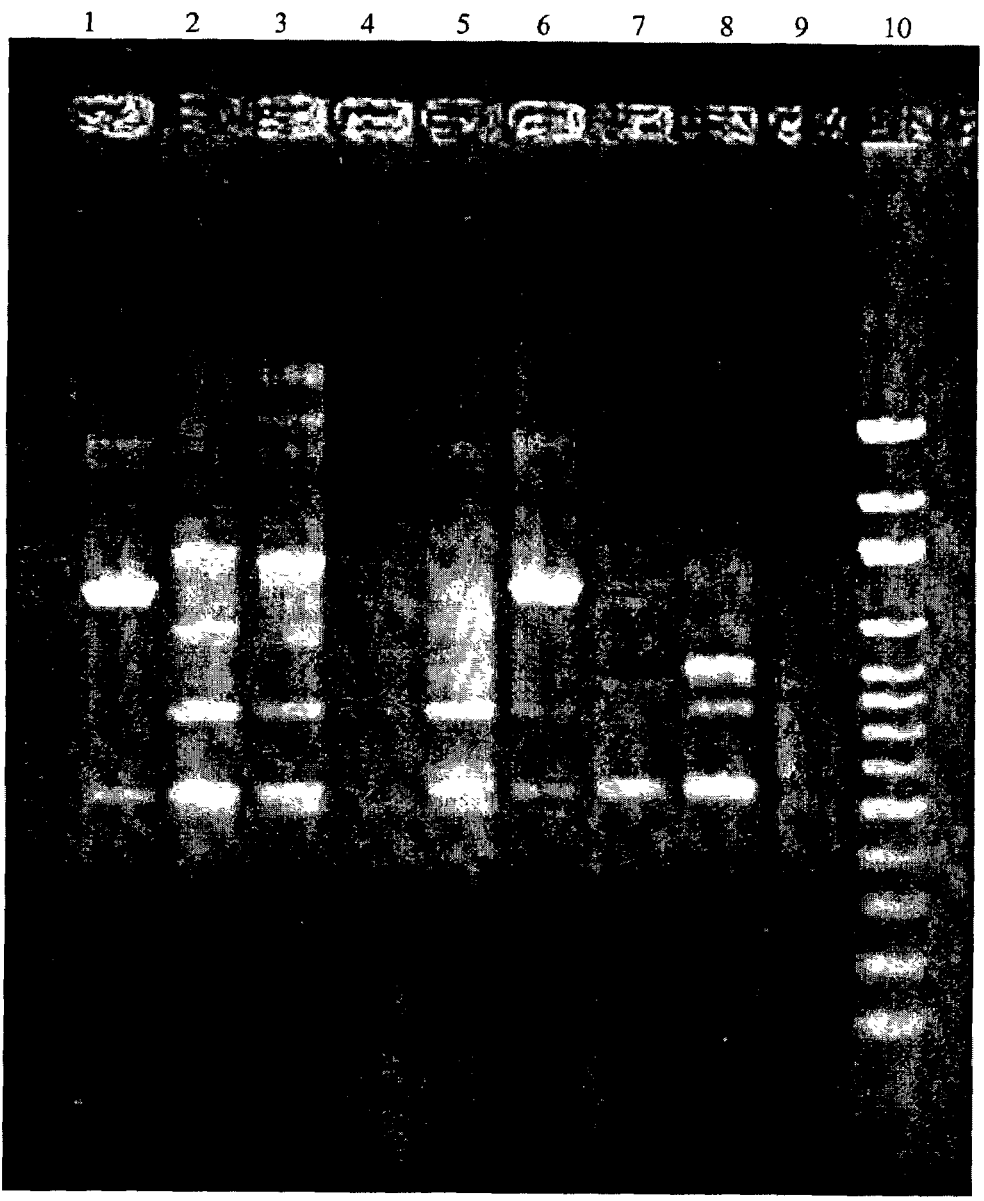

Another aspect of the present invention is to provide a vaccine for birds of the order Galliformes comprising a protective amount of a *Mycoplasma gallisepticum* bacterial strain having a RAPD pattern substantially corresponding to at least one of the band patterns of K5054, as deposited at the ATCC, Patent Deposit Designation PTA-4507, as shown in FIGS. 1, 2, and 3, wherein the band pattern of K5054 in FIG. 1 is generated using as a primer SEQ. ID NO: 4, wherein the band pattern of K5054 is generated using as primers SEQ. ID NO. 5, SEQ. ID NO: 6, and SEQ. ID NO. 7, wherein the band pattern of K5054 is generated using as a primer SEQ. ID NO: 8, and a pharmaceutically acceptable carrier.

Still another aspect of the present invention is a method for protecting a bird of the order Galliformes against *Mycoplasma gallisepticum*, including administering a non-immunopathogenic *Mycoplasma gallisepticum* strain to a bird after the bird hatches, such that the strain persists in the respiratory epithelium of the bird and excludes other *Mycoplasma gallisepticum* strains from the respiratory epithelium.

Yet another aspect of the present invention is a method of administering the vaccine to a bird. Preferably, the vaccine is administered to a bird's respiratory mucosa. More preferably, the protective formulation is administered to chickens. Additionally it may be administered to turkeys.

These and other aspects of the present invention will become apparent to those skilled in the art after a reading of the following description of the preferred embodiments.

BRIEF DESCRIPTION OF THE DRAWINGS/FIGURES

FIG. 1 is a RAPD gel using Charlton's primer.
FIG. 2 is a RAPD gel using three Fan's primers: M16SPCR5', M13F, S1OLIGO3'.
FIG. 3 is a RAPD gel using Geary's 1254 primer.
FIG. 4 is a table showing experimental results.
FIG. 5 is a table showing experimental results.
FIG. 6 is a table showing experimental results.
FIG. 7 is a table showing experimental results.
FIG. 8 is a table showing experimental results.

FIG. 9 is a table showing experimental results.
FIG. 10 is a table showing experimental results.

DETAILED DESCRIPTION OF THE PREFERRED EMBODIMENTS

The present invention provides MG bacteria and derivatives therefrom. The MG bacteria and derivates therefrom according to the invention originate from a passerine strain of MG originating from the house finch *Carpodacus mexicanus*. The strain, now designated K5054, was discovered during an a typical MG outbreak at a commercial turkey operation. Unlike normal MG outbreaks in turkeys, in this particular outbreak few signs of disease appeared. This included sinusitis in breeders as well as serological evidence of infection using ELISA.

In the early stages of this infection, serum plate agglutination (SPA) and hemagglutination inhibition (HI) failed to detect *Mycoplasma gallisepticum*. Tracheal swab cultures and PCR also gave equivocal results and failed to confirm the infection. To enhance the likelihood of obtaining an isolate and to observe the effects of infection, a bioassay was conducted. Susceptible turkeys were inoculated with sinus fluids and monitored for disease and serology. All birds seroconverted, but no clinical signs of disease were observed. However, a single bird exhibited a slightly inflamed sinus. Sinus exudate from this turkey was collected and then inoculated into growth media. Strain K5054 was thus isolated in this fashion.

DNA fingerprinting by the Random Amplified Polymorphic DNA (RAPD) technique and sequencing indicated the strain to be similar to MG strains in house finches but dissimilar to prior art vaccine strains. RAPD patterns of strain K5054, house finch MG, and the vaccine strains (TS-11, 6/85), and field strains (F), and virulent MG strain (R), are shown in FIGS. 1, 2 and 3. S6 is an MG strain used as antigen in the plate agglutination test. A5969 is an MG strain used as antigen in the hemagglutination inhibition test. For the RAPD technique, three different sets of primers were used. The SEQUENCE LISTING is hereby incorporated by reference. In RAPD #1 as seen in FIG. 1 the primer used was SEQ. ID NO: 4. In RAPD #2 as seen in FIG. 2 the primers used were SEQ ID NO: 5, SEQ ID NO. 6, and SEQ. ID NO. 7. In RAPD #3 as seen in FIG. 3 the primer used was SEQ ID NO. 8.

In FIG. 1, the band pattern between House Finch strain (Lane 2) and K5054 (Lane 3) are similar, except that the most predominant PCR product in K5054 is slightly smaller than the corresponding House Finch PCR product. This same product is of an even smaller molecular weight in the vaccine strains. In FIG. 2, the band patterns between House Finch strain (Lane 1) and K5054 (Lane 2) are similar, although K5054 is missing 2 major bands, at approximately 700 kb and 2000 kb, present in the House Finch strain. The other band patterns representing other field or vaccine strains differ more from the House Finch pattern than K5054. In FIG. 3, the RAPD pattern of the House Finch strain (Lane 2) and K5054 (Lane 3) are similar, but differ from the other MG strains. These results identify K5054 as a strain probably derived from House Finch MG. The results also show that the strain differs from other MG strains such as the vaccine strains ts-11, and 6/85, the field strain (F), the virulent MG strain (R), and the antigen strains S6 and A5969.

Partial DNA sequencing of three key genes demonstrated homology between the K5054 strain and the current vaccines strains. The three genes are the PvpA surface cytadhesin, the surface lipoprotein gene, and the mgc1/GapA cytadhesin gene, respectively Sequence ID NO: 1, Sequence ID NO: 2, and Sequence ID NO: 3. The GapA gene sequence in K5054 demonstrated 100% homology with that of 6/85. The PvpA surface cytadhesin gene sequence showed 97.3% homology with that of 6/85, 92.6% homology with that of ts11, 95.2% homology with the F strain, and 98.2% homology with the HF51 strain. The surface lipoprotein gene sequence showed 97.3% homology with that of 6/85, 97.9% with that of ts-11, 97.0% with that of the F strain, and 100% with the HF51 strain.

The MG protective formulation of the present invention is intended for use in birds of the Galliformes order. These include but are not limited chickens and turkeys. Chickens include broilers, reproduction stock and laying stock. Turkeys include reproduction stock and birds for consumption. The protective formulation protects birds by both acting as a vaccine to stimulate protective immunity and by persisting in the respiratory mucosa, especially in the upper respiratory tract of the vaccinated birds and thus excluding virulent field strains from colonizing this area until the birds immune and innate resistances are adequate to exclude these strains from the respiratory mucosa by themselves A preferred embodiment of the invention is an MG protective formulation formed from strain K5054 deposited with the ATCC, Patent Deposit Designation PTA-4507, on Jun. 27, 2002 for birds of the Galliformes order. In a preferred embodiment, the protective formulation is used in chickens. In another preferred embodiment, the protective formulation is used in turkeys. Strains with characteristic serological properties as the said K5054 strain also belong to the invention. This includes passerine infectious strains isolated from house finches. More particularly, strains that are derived from the K5054 strain and retain its particularly favorable protective properties belong to the invention. Preferably the organisms used in the formulation are live.

In one preferred embodiment a protective amount is that amount of MG strain required to colonize the upper respiratory tract of a bird for a sufficient period to provide protection against invasion by virulent wild-type strains. In general, the MG strain according to the present invention needs to colonize the bird's respiratory tract. Optimally, the MG strain should persist in the bird's respiratory tract for at least one year. However, short colonization periods are still useful. For example, colonization of the bird's respiratory tract for even 8 weeks provides protection. In another preferred embodiment, such protective amount is about 1 drop per eye per bird, 1 drop being approximately 0.05 ml, at a concentration of between about $1 \times 10^3$ and about $1 \times 10^6$ color-changing units/ml (ccu/ml). This is equivalent to about 50 to about 50,000 ccu/bird. In an even more preferred embodiment, such protective amount is about 1 drop of a $1 \times 10^5$ ccu/ml solution, corresponding to about 5,000 ccu/bird.

The present invention further includes a method for protecting a bird by administering the MG protective formulation described herein to birds after hatching. Preferably, the formulation is administered during the about first 18 weeks after hatching. More preferably the formulation is administered about at least two weeks after hatching.

The formulation according to the present invention is in a form suitable for administration to the respiratory mucosa. Respiratory mucosal administration means that the formulation is administered such that it is immediately or eventually brought into contact with the bird's respiratory mucosal membranes. Therefore, the formulation can be applied intranasally, orally, and/or intraocularly.

In a preferred embodiment of the invention, the formulation for intranasal or oral administration is in a form suitable for administration by spray, including aerosol, or drinking water, respectively. With these delivery systems, which are less efficient than eyedrop delivery, the actual quantity delivered to each bird is less than via eyedrop delivery. Although administration on an individual bird basis is possible according to the present invention, the formulation is preferably administered by an inexpensive mass application route commonly used for protecting birds from MG, which provides a commercially efficient means for administration.

The spray or aerosol method according to the present invention involves the administration of the MG formulation according to the present invention incorporated in small liquid particles. In the former method, particles usually have an initial droplet size ranging from between about 10 to about 100 microns and in the later method from between about <1 to about 50 microns. For the generation of the small particles, conventional spray-apparatus and aerosol generators can be used, such as the commercially available spray generators for knapsack spray, hatchery spray and atomist spray. Also administration of the formulation through drinking water can be carried out using conventional apparatus.

The formulation according to the present invention containing the MG bacteria can be prepared and marketed in the form of a suspension or in a lyophilized form and additionally can contain a pharmaceutically acceptable carrier or diluent customarily used for such compositions. Carriers include stabilizers, preservatives and buffers commonly known in the art. The formulation is frozen for storage, preferably at –70° C. for optimal storage. Glycerol may be added to the culture media to enhance stability when frozen.

In a preferred embodiment, between about 50 and about 50,000 ccu of the vaccine according to the present invention are administered to a bird. More preferably, about 5,000 ccu of the formulation are administered to a bird. In another embodiment, at least one booster vaccine is administered to the bird at a later time, e.g. between about 12 weeks and about 20 weeks after the initial vaccine administration, if necessary.

Using the live K5054 MG strain deposited with the ATCC, Patent Deposit Designation PTA-4507, and derivatives thereof advantageously provides a live vaccine that persists as a competitive exclusion agent protecting the birds from invasion by wild-type strains. Experimental results in chickens and turkeys show the K5054 strain persists, is non-immunopathogenic and causes minimal disease, and is safe and efficacious, thereby effectively providing a competitive exclusion agent effect. Strains that have similar identifying and functional characteristics to strain K5054 are included in the scope of the present invention. Such strains include derivatives of K5054 and field isolates that have mutated naturally or artificially due to serial passage. These derivatives do not depart from the nature of the invention and are contemplated herein.

Protocol for Growing Mg Strain

MG according to the present invention can be grown in culture according to the following protocol:

Medium: Frey's medium for the isolation of avian mycoplasmas.
Mycoplasma broth base 22.5 g
Dextrose 3 g
Swine serum 120 ml
Yeast Extract 35 ml
Phenol red (1%) 2.5 ml
Thallium acetate (10%)[4] 6 ml
Ampicillin 1 g/liter[4]

Combine reagents and q.s. to 1000 ml with distilled water
A—Thallium acetate and ampicillin can be omitted when working with pure MG cultures, such as in commercial vaccine production.

Adjust pH to 7.8 with 20% NaOH and filter sterilize. Other growth factors and preservatives can be used instead of the ones listed above without departing from the scope of the invention.

For agar medium use 1% of a purified agar such as ion agar #2, Noble agar, or Difco purified agar. All components except serum and ampicillin are sterilized by autoclaving at 121 C for 15 min. Cool to 50 degrees Centigrade and aseptically add serum and ampicillin, which have been pre-sterilized by filtration and warmed to 50 C. Mix and pour plates to a depth of approximately 5 mm.

The following Examples are illustrative of the present invention but are not intended to limit the invention thereto.

EXAMPLE I

Turkey Bioassay

Susceptible turkeys were inoculated with sinus exudate from four different affected commercial turkey flocks. An MG isolation was made from one of the exudates used to challenge the turkeys, it was designated K5054.

Turkeys challenged with sinus exudate from one of the farms (K5054) had very mild clinical signs (one of eight turkeys developed a unilateral sinusitis 42 days post-inoculation) and mild lesions; they seroconverted and developed immunity to subsequent challenge with a virulent MG strain.

EXAMPLE II

Trial A

Four groups of 8 turkeys were challenged with sinus exudate collected from affected commercial turkeys on 4 different farms, one farm having K5054 exudate. A fifth group served as negative controls. The turkeys were observed for clinical signs, bled for serology, and tracheal swabs were obtained for mycoplasma culture. The results of this experiment are shown in FIG. 4.

At 49 days post-challenge, the K5054 sinus exudate inoculated birds (8 principals) were co-mingled with susceptible turkeys (8 contacts). They were observed for clinical signs, bled for serology, and tracheal swabs were obtained for mycoplasma culture after co-mingling. Two of the contact turkeys were necropsied 56 days post-challenge.

The group inoculated with K5054 sinus exudate was the only group that seroconverted. They were positive at 21 days post inoculation and remained positive until the end of the study. One of eight turkeys inoculated with K5054 sinus exudates exhibited a unilateral sinusitis at 49 days post inoculation. K5054 was re-isolated from the sinus exudate of that turkey. This was the only re-isolation of K5054 during the study. The results show persistence of and mild disease symptoms caused by the K5054 strain in turkeys.

Trial B

The remaining turkeys, 8 principals and 6 contacts, from Trial A were used in Trial B. Eighty-eight days after the K5054 sinus exudate inoculation, 7 of the turkeys (4 principals and 3 contacts) were challenged with R strain of MG by aerosol. The 7 remaining turkeys (4 principals and 3 contacts) were used as controls. All of the turkeys were necropsied 10 days after the R strain challenge. They were bled for serology, and tracheal and air sac swabs were obtained for culture. Tracheal sections were fixed in formalin for tracheal mucosa thickness measurements.

The results of Trial B are summarized in FIG. 5. The turkeys that were previously inoculated with K5054 had no air sac lesions following challenge with R strain. The mean tracheal mucosa thickness for these turkeys was also significantly less than the challenge controls and not significantly different from the unchallenged turkeys. R strain was not re-isolated from these turkeys after challenge. The results show that K5054 protects turkeys against MG infection.

EXAMPLE III

Inoculation with K5054 sinus exudate resulted very little clinical reaction in the turkeys in the bioassay. To further explore the safety of the K5054 strain preliminary investigations were conducted in chickens and turkeys. The birds were challenged by coarse spray with K5054 propagated in Frey's medium.

K5054 challenge in chickens and turkeys resulted in seroconversion with few indications of disease.

Trial 1: Safety in Chickens

Commercial layer-type chickens were challenged with K5054 by coarse spray, ts-11 and R strain. They were evaluated by serology, gross evaluation of air sac lesions and measurement of the thickness of the tracheal mucosa 10 days post challenge. The results of this experiment are depicted in FIG. 6, and FIG. 7.

| | Experimental Design | | |
|---|---|---|---|
| Group | Number of Birds | Challenge Method | Titer (ccu/ml) |
| Ts-11 | 16 | Eyedrop | $1.11 \times 10^4$ |
| K5054 | 16 | Coarse spray | $1.59 \times 10^8$ |
| R | 16 | Coarse spray | $1.91 \times 10^8$ |
| Negative Controls | 16 | NA | NA |

The Ts-11 and K5054 groups both resulted in no gross air sac lesions. The mean tracheal mucosa thicknesses for these groups were not significantly different from the negative controls but significantly less than the challenge controls.

Trial 2: Safety in Turkeys

Turkeys acquired from a commercial source were inoculated with K5054 and R strain by coarse spray at 4 weeks of age. They were necropsied 10 days later along with a negative control group. The results are depicted in FIG. 8.

| | Experimental Design | | |
|---|---|---|---|
| Group | Number of Birds | Challenge Method | Titer (ccu/ml) |
| K5054 | 15 | Coarse spray | $7.74 \times 10^8$ |
| R | 15 | Coarse spray | $8.42 \times 10^8$ |
| Negative Controls | 15 | NA | NA |

The mean air sac lesion score and mean tracheal mucosa thickness for the K5054 group were significantly less than the challenge controls and not significantly different from the negative controls.

EXAMPLE IV

Efficacy

Turkeys in the bioassay that were inoculated with K5054 sinus exudates and later challenged with R strain showed excellent protection against disease. The efficacy of K5054 as a live vaccine for MG was evaluated by challenging chickens and turkeys that had been previously inoculated with K5054 with a virulent MG strain (R).

Vaccination with K5054 resulted in a significant reduction in MG lesions associated with disease following challenge with R strain.

Trial 1: Efficacy in Chickens

Commercial layer-type chickens were inoculated with K5054 or ts-11. They were challenged 5 weeks later with R strain (coarse spray). 10 days post challenge they were evaluated by serology, gross evaluation of air sac lesions and measurement of the thickness of the tracheal mucosa. The experimental design is depicted below. The results of this trial are depicted in FIG. 9.

| | Experimental Design: | | |
|---|---|---|---|
| Vaccine | Challenge | Group | Number of Birds |
| Ts-11 | R | Ts-11 Challenged | 40 |
| | No Challenge | Ts-11 Controls | 10 |
| K5054 | R | K5054 Challenged | 40 |
| | No Challenge | K5054 Controls | 10 |
| No vaccine | R | Challenge Controls | 40 |
| | No Challenge | Negative Controls | 32 |

The Ts-11 and K5054 groups resulted in mean air sac lesion scores that were significantly different from the challenged controls. The mean tracheal mucosa measurements for the vaccinated groups were also significantly different from that of the challenge controls but not significantly different from the negative control group.

Trial 2: Efficacy in Turkeys 18 turkeys previously vaccinated with K5054 were challenged with R strain ($1.38 \times 10^9$ ccu/ml) by coarse spray 6 weeks post vaccination. They were necropsied 10 days later along with a negative control group. The turkeys were evaluated by serology, air sac lesions and tracheal mucosa thickness. The results of this trial are depicted in FIG. 10.

The mean air sac lesion score and mean tracheal mucosa thickness for the group inoculated with K5054 were significantly different from the challenged controls but not from the negative controls.

Although preferred and alternative embodiments of the present invention have been described in the foregoing, it will be understood by those skilled in the art that the invention is not limited to the embodiments disclosed, but is capable of numerous modifications, rearrangements and substitutions of the component parts and elements without departing from the spirit of the invention.

Certain modifications and improvements will occur to those skilled in the art upon a reading of the foregoing description. All modifications and improvements have been deleted herein for the sake of conciseness and readability but are properly within the scope of the following claims.

We claim:

1. A vaccine for birds of the order Galliformes comprising an amount of the K5054 *Mycoplasma gallisepticum* strain, deposited at the ATCC under Patent Deposit Designation PTA-4507, sufficient to protect the birds disease induced by *Mycoplasma gallisepticum*, and a pharmaceutically acceptable carrier.

2. The vaccine of claim 1, wherein the protective amount is that amount required for the K5054 *Mycoplasma gallisepticum* strain to colonize the upper respiratory tract of the bird.

3. The vaccine of claim 1, wherein the protective amount is between about 50 and about 50,000 ccu/bird.

4. The vaccine of claim 1, wherein the protective amount is about 5,000 ccu/bird.

5. An essentially biologically pure culture of the K5054 *Mycoplasma gallisepticum* strain deposited at the ATCC under Patent Deposit Designation PTA-4507.

6. A method for protecting a bird of the order Galliformes against disease induced by *Mycoplasma gallisepticum*, comprising administering to the bird after the bird hatches the K5054 *Mycoplasma gallisepticum* strain, deposited at the ATCC under Patent Deposit Designation PTA-4507, such that said strain persists in the respiratory epithelium of the bird and excludes other *Mycoplasma gallisepticum* strains from the respiratory epithelium.

* * * * *

UNITED STATES PATENT AND TRADEMARK OFFICE
CERTIFICATE OF CORRECTION

PATENT NO. : 7,217,420 B2
APPLICATION NO. : 10/194180
DATED : May 15, 2007
INVENTOR(S) : S.H. Kleven et al.

Page 1 of 1

It is certified that error appears in the above-identified patent and that said Letters Patent is hereby corrected as shown below:

| COLUMN | LINE | ERROR |
|---|---|---|
| On Title Page Item (74) pg. 1, col. 1 | Attorney, Agent, or Firm | "Christensen, O'Connor Johnson Kindess PLLC" should read --Christensen O'Connor Johnson Kindness PLLC-- |
| 3 | 10 | "forts-11," should read --for ts-11,-- |
| 13 (Claim 1, | 53 line 4) | "protect the birds disease" should read --protect the birds from disease-- |

Signed and Sealed this

Second Day of October, 2007

JON W. DUDAS
*Director of the United States Patent and Trademark Office*